United States Patent
Chiang et al.

(10) Patent No.: US 11,521,317 B2
(45) Date of Patent: Dec. 6, 2022

(54) METHOD FOR ANALYZING TISSUE SPECIMENS

(71) Applicant: JelloX Biotech Inc., Hsinchu (TW)

(72) Inventors: Ann-Shyn Chiang, Hsinchu (TW); Dah-Tsyr Chang, Hsinchu (TW); Jia-Ling Yang, Hsinchu (TW); Yen-Yin Lin, Hsinchu (TW); Yu-Chieh Lin, Hsinchu (TW)

(*) Notice: Subject to any disclaimer, the term of this patent is extended or adjusted under 35 U.S.C. 154(b) by 342 days.

(21) Appl. No.: 16/891,100

(22) Filed: Jun. 3, 2020

(65) Prior Publication Data

US 2020/0388031 A1 Dec. 10, 2020

Related U.S. Application Data

(60) Provisional application No. 62/856,742, filed on Jun. 4, 2019.

(51) Int. Cl.
*G06T 7/00* (2017.01)
*G01N 1/30* (2006.01)
(Continued)

(52) U.S. Cl.
CPC ............ *G06T 7/0012* (2013.01); *G01N 1/30* (2013.01); *G01N 33/533* (2013.01); *G06T 11/60* (2013.01);
(Continued)

(58) Field of Classification Search
CPC ............... G06T 7/0012; G06T 11/60; G06T 2207/10056; G06T 2207/10064;
(Continued)

(56) References Cited

U.S. PATENT DOCUMENTS 10,591,392 B2 * 3/2020 Torres .............. G01N 33/4833
2010/0144002 A1 6/2010 Donndelinger
(Continued)

FOREIGN PATENT DOCUMENTS

| CN | 108796041 A | 11/2018 |
| TW | 412637 B | 11/2000 |
| TW | I291630 B | 12/2007 |

OTHER PUBLICATIONS

Choi et al. "Three-Dimensional Quantitative Analysis of Cell Nuclei for Grading Renal Cell Carcinoma." Proceedings of 7th International Workshop on Enterprise Networking and Computing in Healthcare Industry, Jun. 23, 2005, pp. 179-18 (Year: 2005).*
(Continued)

*Primary Examiner* — Jon Chang
(74) *Attorney, Agent, or Firm* — OPES IP Consulting Co. Ltd

(57) ABSTRACT

Provided is a method for analyzing a tissue specimen, including treating a tissue specimen with an aqueous clearing agent and with at least two fluorescent probes to obtain a cleared and labeled tissue specimen; imaging the cleared and labeled tissue specimen to generate a three-dimensional (3D) image of the tissue specimen; preparing a stained tissue section from the cleared and labeled tissue specimen; capturing a reference two-dimensional (2D) image of the stained tissue section; matching the reference 2D image with the 3D image to extract from the 3D image a series of 2D image slices including a corresponding 2D image slice that corresponds to the reference 2D image; and determining at least one pathological score for each of the series of 2D image slices and reporting the presence or absence and the extent of the disease based on the pathological scores. The method can improve the accuracy of histopathologic diagnosis.

20 Claims, 8 Drawing Sheets

(51) Int. Cl.
*G01N 33/533* (2006.01)
*G06T 11/60* (2006.01)

(52) U.S. Cl.
CPC .................... *G01N 2800/60* (2013.01); *G06T 2207/10056* (2013.01); *G06T 2207/10064* (2013.01); *G06T 2207/30024* (2013.01); *G06T 2207/30096* (2013.01)

(58) Field of Classification Search
CPC ........... G06T 2207/30024; G06T 2207/30096; G01N 1/30; G01N 33/533; G01N 2800/60
See application file for complete search history.

(56) References Cited

U.S. PATENT DOCUMENTS

| | | | |
|---|---|---|---|
| 2012/0196320 A1* | 8/2012 | Seibel | G01N 1/30 348/E13.02 |
| 2013/0023008 A1 | 1/2013 | Becker et al. | |
| 2020/0224129 A1* | 7/2020 | Lai | C11D 7/3209 |

OTHER PUBLICATIONS

Samarabandu et al. "Three-Dimensional Structural Analysis from Biological Confocal Images." Proc. SPIE 1556, Scanning Microscopy Instrumentation, doi: 1117/12.134898, Feb. 1, 1992, pp. 154-163 (Year: 1992).*

Office Action and search report from the Taiwan Intellectual Property Office, Nov. 4, 2021.

* cited by examiner

METHOD FOR ANALYZING TISSUE SPECIMENS

CROSS-REFERENCE TO RELATED APPLICATIONS

This application claims priority of Provisional Application No. 62/856,742, filed on Jun. 4, 2019, the content of which is incorporated herein in its entirety by reference.

BACKGROUND OF THE INVENTION

1. Field of the Invention

The present invention relates to a method for histopathologic diagnosis. Particularly, the present invention relates to a method for analyzing tissue specimens by performing three-dimensional (3D) and two-dimensional (2D) imaging of the same tissue specimen and utilizing the 3D image data to aid 2D image-based histopathologic diagnosis.

2. The Prior Arts

Histological examination of tissues is the standard approach to analyze tissue architecture and cell morphology and has been employed in diagnosing a variety of diseases, including cancers. The typical procedure for histological examination includes the steps of fixing a biopsy specimen or tissue specimen, embedding the tissue specimen in embedding materials to generate a tissue block, slicing the block into thin sections, staining the thin sections with dyes such as haematoxylin and eosin (H&E) to prepare stained sections, and capturing 2D microscopic images of the stained sections for visual analysis.

One major problem encountered by pathologists when diagnostic decisions were made based on the traditional histological examination is the representativeness of samples (i.e., stained sections) and the quality of sample images. Factors interfering histological examination and thus reducing the accuracy of diagnostic decisions include tissue distortion from sample preparation, particularly due to specimen dehydration and slicing, and loss of morphological information due to slicing and tissue discontinuity.

Though techniques associated with 3D imaging of the body such as magnetic resonance imaging (MRI) and computed tomography (CT) have been applied widely to monitor a diseased portion of the body directly, clinical diagnosis still relies on tissue sections that reveal detailed information. On the other hand, to minimize the information loss due to tissue discontinuity, several computer-based methods have been utilized to convert 2D images of stained tissue sections into virtual 3D image stacks of the tissue specimen. However, it is challenging to fill the gaps formed between the discontinuous tissue sections and to eliminate the artifacts originated from the tissue preparation process.

Accordingly, it is necessary to develop a new strategy to improve the conventional histological examination process to achieve more accurate diagnosis.

SUMMARY OF THE INVENTION

The present invention concerns a method of analyzing tissue specimens to assist diagnosis of a disease in a subject. The method includes at least the steps of: (a) treating a tissue specimen from a subject with an aqueous clearing agent and with at least two fluorescent probes for labeling cell membrane and cell nuclei so as to obtain a cleared and labeled tissue specimen; (b) imaging the cleared and labeled tissue specimen to generate a three-dimensional (3D) image of the tissue specimen; (c) preparing a stained tissue section from the cleared and labeled tissue specimen; (d) capturing a reference two-dimensional (2D) image of the stained tissue section; (e) matching the reference 2D image with the 3D image to extract from the 3D image a series of 2D image slices, wherein one of the series of 2D image slices is a corresponding 2D image slice, and the corresponding 2D image slice is least different in morphology from the reference 2D image comparing to other 2D image slices in the series of 2D image slices; and (f) determining at least one pathological score for each 2D image slice in the series of 2D image slices and reporting the presence or absence and the extent of a disease based on the pathological scores.

In certain embodiments of the invention, the aqueous clearing agent used for tissue clearing has a refractive index of 1.33-1.55, preferably 1.40-1.52, and more preferably 1.45-1.52. The aqueous clearing agent may include an ingredient selected from the group consisting of glycerol, histodenz, formamide, triethanolamine, meglumine diatrizoate, and combinations thereof. Treatment with such aqueous clearing agent, which takes no more than 12 hours, causes a tissue specimen with a thickness of at least 200 μm to become sufficiently transparent while preventing tissue shrinkage or deformation and eliminating lipid removal. Since the structural integrity of the cleared tissue specimen is well preserved, the microscopic images obtained thereafter provide more accurate morphological information. Moreover, fluorescent labeling of cell membrane and membrane associated proteins are compatible with such clearing agent, allowing detection of various marker proteins for many diseases, particularly for cancers.

In certain embodiments of the invention, the 3D image is a 3D composite image generated from a plurality of successive 2D images, which are captured for the cleared and labeled tissue specimen using a fluorescence imaging system including a laser scanning confocal microscope.

In certain embodiments of the invention, the matching of step (e) is accomplished by comparing a reference feature vector of the reference 2D image to a corresponding feature vector of each 2D image slice in the series of 2D image slices. The reference feature vector or the corresponding feature vector may describe cell shape, cell nuclei distribution, or combinations thereof.

In certain embodiments of the invention, in step (a) the tissue specimen is further treated with another fluorescent probe to label at least one organelle or at least one biomolecule such as a protein characteristic of the disease. Based on this labeling, the biomolecule or organelle serving as the disease marker may be quantified to yield the pathological score for each 2D image slice in the series of 2D image slices. In certain embodiments, the presence of the disease is reported when the difference between the pathological scores of any two of the series of the 2D image slices is within a predetermined range.

In certain embodiments of the invention, the disease is neoplasm, for example, breast cancer, lung cancer, gastric cancer, liver cancer, gallbladder cancer, pancreatic cancer, colon cancer, colorectal cancer, prostate cancer, cervical cancer, ovarian cancer, kidney cancer, bladder cancer, glioma, retinoblastoma, melanoma, and head and neck cancers.

In another aspect, a system for assisting disease diagnosis is also provided herein. The system includes a storage medium storing a plurality of instructions readable by a processor. The instructions, when executed by the processor, facilitates performance of operations, including (s1) matching a reference two-dimensional (2D) image of a stained tissue section prepared from a tissue specimen with a three-dimensional (3D) image of the tissue specimen so as to extract from the 3D image a series of 2D image slices, wherein one of the series of 2D image slices is a corresponding 2D image slice, and the corresponding 2D image slice is least different in morphology from the reference 2D image comparing to other 2D image slices in the series of 2D image slices; and (s2) determining at least one pathological score for each of the 2D image slices and reporting the presence or absence and the extent of a disease based on the pathological scores.

The method of the present invention generates and matches a 3D image of a tissue specimen with a conventional 2D image of a section of said specimen in order to extract a series of 2D image slices corresponding to the conventional 2D image and obtain pathological scores that can be used to verify histopathological results. Comparing to the conventional histopathological diagnosis, which is made by examination of 2D images of tissue sections, the disclosed method takes advantage of additional information extracted from the 3D image of the original tissue specimen to yield a more reliable diagnostic report. Therefore, physicians can make more accurate diagnosis and determine appropriate treatments by using the method disclosed herein.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENT

Figure 1:
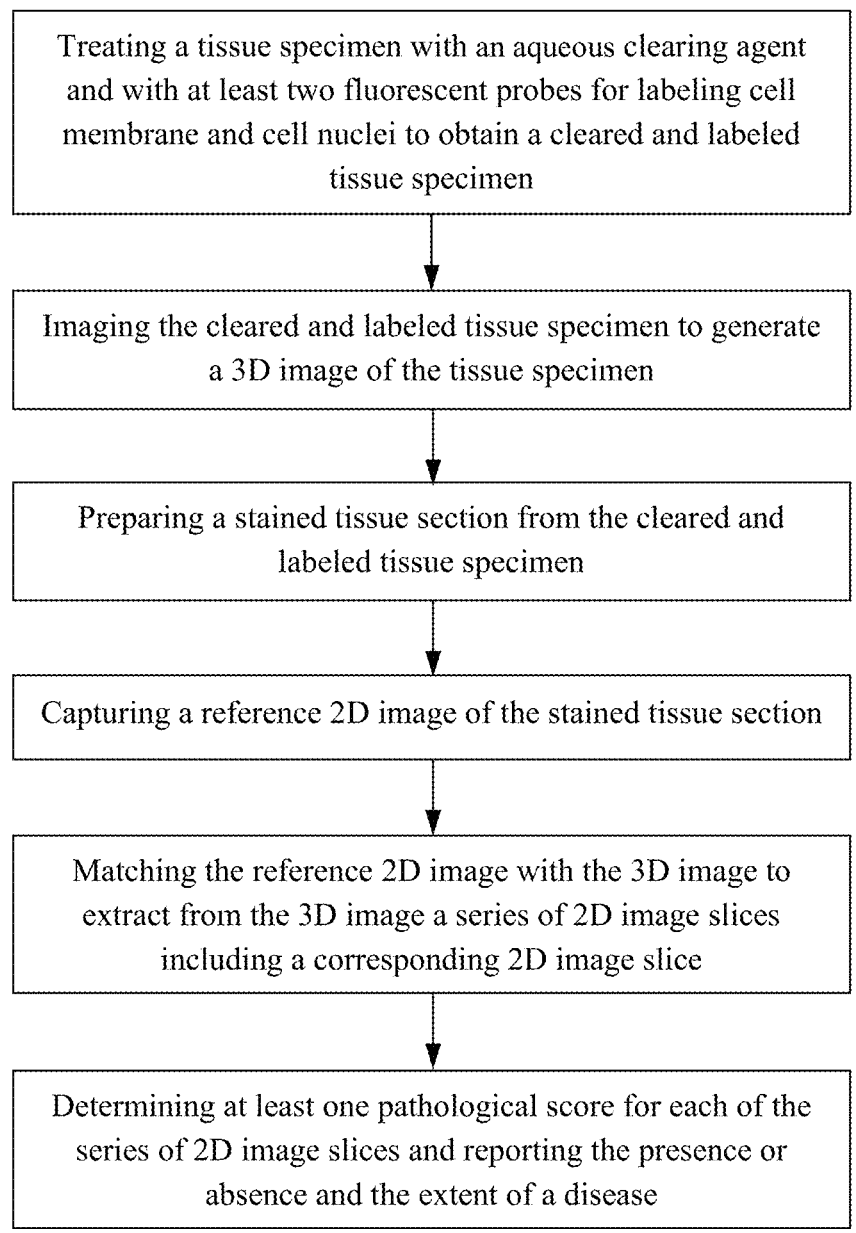
FIG. 1 is a flow chart illustrating the steps of the method of the invention.

The present invention is further explained in the following embodiments and examples. It is understood that the examples given below do not limit the scope of the invention, and it will be evident to those skilled in the art that modifications can be made without departing from the scope of the appended claims.

Unless defined otherwise, all technical and scientific terms and abbreviations used herein have the same meaning as commonly understood by a person skilled in the art to which this invention pertains.

Definition

As used herein, the singular forms "a", "an" and "the" include plural referents unless the context clearly indicates otherwise.

Numerical quantities given herein are approximate, and experimental values may vary within 20 percent, preferably within 10 percent, and most preferably within 5 percent. Thus, the terms "about" and "approximately" refer to within 20 percent, preferably within 10 percent, and most preferably within 5 percent of a given value or range.

As used herein, "wt %" or "% w/w" refers to % by weight of a composition.

As used herein, the term "image" refers to a two-dimensional (2D) or three-dimensional (3D) microscopic image of a biological tissue specimen or a section of the specimen. The image may be captured with any imaging system including a microscope.

As used herein, the term "subject" refers to a mammal in need of diagnosis for diseases. The subject may be human or non-human, such as a primate, murine, dog, cat, cow, horse, rabbit, pig or the like.

The term "disease" as used herein refers to any disorder of structure or function in one subject that produces symptoms or abnormal tissue morphology, which can be detected by conventional histological techniques. One example of diseases is neoplasm (also called tumor), which is characterized by unregulated new growth of cells. Said tumors include benign (non-cancerous) and malignant (cancerous) tumors, defined by the low or high potentiality of the tumor cells to spread or invade other parts of the body, respectively. Examples of malignant tumors, also called cancers, include but not limited to carcinoma, sarcoma, lymphoma, and blastoma. More specifically, the cancers include breast cancer, lung cancer, small-cell lung cancer, non-small cell lung cancer, gastric cancer, liver cancer, gallbladder cancer, pancreatic cancer, colon cancer, colorectal cancer, prostate cancer, cervical cancer, ovarian cancer, kidney cancer, bladder cancer, glioma, retinoblastoma, melanoma, and various types of head and neck cancers.

The expression "extent of disease" as used herein refers to the severity or progression of a disease, which can be judged by the symptoms of a disease or the level of cellular or histological abnormalities. One example is the extent of a tumor or a cancer. The extent of a cancer may be described as the stage or the grade of a cancer. The stage of a cancer may be determined based on the size of a tumor, and where and how deeply a tumor has spread. A standard system for describing a cancer's progression is the TNM staging system set by America Joint Committee on Cancer (AJCC), where the T refers to the size of a tumor, the N tells the number of lymph nodes involved with cancer, and the M describes whether or not the cancer has spread to other organs in the body. Typically, a cancer falls within one of four stages (stages I-IV), whereas stage 0 indicates no cancer is present. For example, breast cancer is generally categorized into stage I, indicating the size of tumor is no more than 2 cm but no cancer cells are found in the lymph nodes; stage II, indicating the size of tumor is from 2 cm to 5 cm and/or cancer has spread to lymph nodes; stage III, indicating the size of tumor is more than 5 cm and/or cancer in the lymph nodes is extensive; and stage IV, indicating cancer has spread to another organ in the body. On the other hand, the grade of a cancer may be determined based on the how abnormal the cancer cells look, and how fast the cancer is likely to grow or spread.

The method of the invention for assisting diagnosis of a disease in a subject begins with a tissue sample or specimen collected from the subject to be diagnosed. Said subject, either already diseased or prone to disease, is usually subjected to a biopsy, which is a procedure to remove a piece of tissue from an individual's body such that the specimen can be subsequently analyzed to identify the presence and the extent of a disease. Various types of biopsies can be performed to obtain a tissue specimen to be examined following the disclosed method. Examples of biopsies include skin biopsy, endoscopic biopsy, needle biopsy, bone marrow biopsy, and surgical biopsy.

Accordingly, the tissue specimen may be a portion of the skin, cornea, hair, retina, breast, heart, lung, bronchi, stomach, liver, spleen, pancreas, intestine, colon, kidney, bladder, prostate, ovary, cervix, bone, muscle, or brain.

As shown in FIG. 1, the method disclosed herein includes at least the steps of: (a) treating a tissue specimen from a subject with an aqueous clearing agent and with at least two fluorescent probes for labeling cell membrane and cell nuclei to obtain a cleared and labeled tissue specimen; (b) imaging the cleared and labeled tissue specimen to generate a 3D image of the tissue specimen; (c) preparing a stained tissue section from the cleared and labeled tissue specimen; (d) capturing a reference 2D image of the stained tissue section; (e) matching the reference 2D image with the 3D image to extract from the 3D image a series of 2D image slices, wherein one of the series of 2D image slices is a corresponding 2D image slice, and the corresponding 2D image slice is least different in morphology from the reference 2D image comparing to other 2D image slices in the series of 2D image slices; and (f) determining at least one pathological score for each 2D image slice in the series of 2D image slices and reporting the presence or absence and the extent of the disease based on the pathological scores.

According to FIG. 1, prior to the first image acquisition of step (b), the tissue specimen is treated with an aqueous clearing agent to obtain a cleared tissue specimen (step (a) of the disclosed method). Typically, a tissue specimen with a thickness of more than about 5-10 µm is too thick to be observed clearly through a conventional wide-field microscope, because the view would be the sum of a sharp image of an in-focus region and blurred images of the out-of-focus regions. To obtain a high-resolution view of thick specimens, confocal microscopy or multiphoton microscopy is employed in the first image acquisition to avoid image blurring owing to large amounts of out-of-focus light, resulting in an depth resolution (the resolution in the depth direction or z direction) or axial resolution of about less than 2 µm. Nevertheless, even when a confocal microscope or multiphoton microscope is utilized, thick specimens with a thickness of more than 100 µm still need to be sliced into thin sections prior to examination of cellular features due to the limitations of such microscopes in light penetration depth (about 100-200 µm). To minimize the need for physical sectioning of tissue and the associated morphological distortion, the step of tissue clearing is included in the disclosed method. The aqueous clearing agent includes at least one water-soluble chemical with a refractive index closer to that of proteins and lipids. The aqueous clearing agent renders the tissue optically clear or transparent by homogenization of the various refractive indices of a tissue, resulting in reduced light scattering and improved light penetration. Hence, tissue clearing allows nearly no physical tissue sectioning prior to the first image acquisition of thick tissue specimens, and thus reduces the possible artifacts resulting from tissue stretching, bending, and tearing.

In certain preferred embodiments, the aqueous clearing agent has a refractive index of 1.33-1.55, preferably 1.40-1.52, and more preferably 1.45-1.52. The aqueous clearing agent may be prepared by adding in water or phosphate buffered saline (PBS; for example, 137 mM sodium chloride, 2.7 mM potassium chloride, 7.7 mM di sodium hydrogen phosphate, and 1.47 mM potassium dihydrogen phosphate dissolved in water, pH 7.4) an ingredient selected from the group consisting of glycerol, histodenz, formamide, triethanolamine, meglumine diatrizoate, and combinations thereof. The final concentration of said ingredient in the aqueous clearing agent may vary between 30-70 wt %. Tissue clearing with such aqueous clearing agent may be carried out at room temperature for 2 to 12 hours, preferably for 2 to 8 hours, and more preferably for 2 to 4 hours.

In one embodiment of the invention, the cleared tissue specimen to be examined has a thickness of between 50 µm and 75 µm, between 75 µm and 100 µm, between 100 µm and 125 µm, between 125 µm and 150 µm, between 150 µm and 175 µm, between 175 µm and 200 µm, between 200 µm and 225 µm, or between 225 µm and 250 µm. Preferably, the cleared tissue specimen has a thickness of more than 250 µm to less than 300 µm. More preferably, the cleared tissue specimen has a thickness of more than 300 µm.

In addition to treatment with the aqueous clearing agent, the tissue specimen is also treated with at least two fluorescent probes to obtain a labeled tissue specimen (step (a) of the disclosed method). The fluorescent probes are fluorescent molecules that recognize a target molecule or structure and emit light upon illumination. In one embodiment, the fluorescent probe is a fluorophore that specifically binds to a cell substructure, such as cell membrane, or specifically marks an organelle, such as cell nucleus and mitochondria. Examples of the fluorophore include nuclear probes such as propidium iodide (PI), 4',6-diamino-2-phenylindole (DAPI), and SYTO-series of dyes (e.g., SYTO 11 and SYTO 16 purchased from Thermo Fisher Scientific); and membrane lipid probes such as Di series of dyes (e.g., DiD and DiR purchased from Invitrogen) and PKH series of dyes (e.g., PKH26 and PKH67 purchased from Merck). In another embodiment, the fluorescent probe is a conjugate including a fluorophore covalently conjugated with a molecular probe capable of specifically binding to a biomolecule such as a protein with a particular amino acid sequence, a nucleic acid with a particular nucleotide sequence, or lipids of cell membrane. Examples of the molecular probes include but not limited to an antibody, an antibody fragment, a lectin, and a nucleic acid probe. The molecular probes are commercially available or may be prepared by methods known in the art.

In certain embodiments, step (a) is accomplished by separately contacting the tissue specimen with the aqueous clearing agent and the fluorescent probes. Tissue clearing may be carried out prior to or after tissue labeling. In other embodiments, the clearing and labeling are integrated, for example, the tissue specimen is contacting with a first aqueous clearing agent, and then with fluorescent probes, and finally with a second aqueous clearing agent.

The tissue specimen to be cleared and labeled may be either fresh or archival. In one embodiment, the tissue specimen is collected immediately from a portion of a patient's body, such as a solid tumor, and thus is in a fresh state. In another embodiment, the tissue specimen has been processed according to sample preparation methods well-known to one skilled in the art and is referred to as an archival specimen. The sample preparation methods may include the steps of fixation, dehydration, infiltration, and embedding. Fixation is a process to prevent decay and preserve tissue morphology in which a tissue specimen is immersed in a fixative such as formalin (4% formaldehyde by mass in buffered saline) at room temperature for typically 4-48 hours, depending on the size of the specimen. Dehydration is a process to remove water from the specimen by treating a fixed specimen with increasing concentrations of a dehydrant, for example, treatment with 70%, 95%, and 100% of an alcohol such as ethanol, followed by treatment with xylene. Infiltration is a process to allow an embedding medium such as wax to permeate the specimen. One example of infiltration is placing a dehydrated specimen in a mixture of xylene and a molten wax such as paraffin wax heated to 56-60° C. Embedding is accomplished by transferring an infiltrated specimen in an embedding container, where the embedding medium such as molten paraffin wax is subsequently introduced around the specimen and cooled to form a hard block of tissue (also called tissue block). The archival specimen processed by fixation with formalin and embedding in paraffin is referred to as FFPE-treated.

In the case where the tissue specimen is fresh, the specimen may further be fixed with a fixative such as formalin at room temperature for 6 to 12 hours prior to the clearing and labeling step. Alternatively, when a FFPE-treated specimen is to be examined, it may be deparaffinized with xylene and alcohol at room temperature for 2 hours and 4-6 hours, respectively, prior to the clearing and labeling step. The specimen, either fresh or FFPE-treated and further deparaffinized, may be embedded in a hydrogel, which provides physical support to the specimen during tissue clearing and labeling. In one embodiment, the hydrogel is an agarose gel prepared from a warm aqueous solution containing 1-4% w/w agarose. In another embodiment, the hydrogel is prepared from a water dispersion of at least one natural or synthetic polymer which solidifies upon change in temperature, pH, salts, or irradiation. Examples of said polymer include but not limited to alginate, hyaluronates, and acrylamide-based polymers.

Moreover, in the case where conjugates such as fluorophore-conjugated antibodies are used as the fluorescent probes for labeling, the tissue specimen is permeabilized to ensure the access of the probes to the target biomolecules. Permeabilization may be carried out at room temperature with a solution containing low concentrations (e.g., 0.1-2 wt %) of a detergent such as Triton-X 100 or Tween 20.

Once the cleared and labeled tissue specimen with a proper thickness is obtained, it is imaged to generate a 3D image of the tissue specimen. In certain embodiments, the 3D image is a 3D composite image produced from a plurality of successive 2D images of optical sections of the cleared and labeled tissue specimen. The term "optical section" means a plane of an object (e.g., a tissue specimen) brought into view by adjustment of the focus of a microscope, usually by adjusting the distance between the observed specimen and an objective of the microscope. In other words, the successive 2D images of optical sections of the tissue specimen are the cross-sectional images of the tissue specimen at a different depth from a reference surface, such as the top surface or bottom surface of the specimen.

Imaging of the cleared and labeled tissue specimen may be carried out with a fluorescence imaging system including a fluorescence microscope, an image capture device connected to the fluorescence microscope, and a computer connected to the fluorescence microscope and the image capture device, both of which may be operated by the computer. The fluorescence microscope may be a laser scanning confocal microscope (LSCM), for example, FLUOVIEW-series (Olympus, Japan) or LSM-series (Zeiss, Germany), a two-photon microscope, a three-photon microscope, a spinning disk confocal microscope, a line-scanning confocal microscope, or a light-sheet microscope. The fluorescence microscope typically includes a light source, a set of lens, and a motorized sample stage for holding a specimen and moving the specimen in both the horizontal direction (the direction of x or y axis) and the vertical direction (the direction of z-axis). The light source of LSCM is a laser, for example, argon ion laser and helium/neon laser, which excites the fluorescent probes. The set of lens includes a series of objectives, such as a 20× (magnification) objective and a 40× objective. The image capture device such as a camera includes a light detector, which detects the incident photons and converts them into electrical signals transmitted to the computer for generating a digital 2D image. Examples of the light detector includes a charge-coupled device (CCD) image sensor, a photomultiplier tube (PMT) detector, and a complementary metal-oxide semiconductor (CMOS) sensor. The computer is installed with an application software through which a user controls the operation of the fluorescence microscope and the image capture device.

In certain embodiments of the invention, a LSCM system is used to capture 2D images of different focal planes in the z direction within the tissue specimen. In brief, the specimen is illuminated in a scanning manner with a focused beam of light (e.g., visible light). The emitted fluorescence then passes through the optics of the microscope and only in-focus fluorescence reaches the detector of the camera, from which electrical signals corresponding to the light intensity of each point of one predetermined optical section are transmitted to the computer. Finally, a digitized 2D image of the predetermined optical section is generated and the digital data of the 2D image is stored in a memory unit of the computer. By adjusting the focal plane of the microscope, a plurality of 2D images of successive optical sections of the specimen are captured and digitally recorded. During the first image acquisition, the digital images stored in the computer can be displayed on a monitor connected to the computer for immediate examination. In one embodiment, the first image acquisition is completed when all optical sections within the whole specimen are imaged. In another embodiment, the first image acquisition is terminated once the images of part of the specimen are obtained.

The digital 2D images of the tissue specimen are used as the input data to generate a 3D composite image or a 3D model of the tissue specimen, a process called 3D reconstruction. This process is implemented by a computer using a varieties of 3D reconstruction algorithms known in the art, such as trilinear interpolation, nearest neighbor interpolation, and tricubic interpolation. In certain embodiments, the software provided with the LSCM system such as FLU-OVIEW-series (Olympus, Japan) or LSM-series (Zeiss, Germany) can perform 3D reconstruction. Through this process, the successive 2D images are aligned and stitched to one another to create the 3D composite image of the tissue specimen. In certain embodiments, digital filtering and deblurring such as deconvolution are applied to create a 3D composite image with enhanced resolution.

After the first image acquisition is completed, the cleared and labeled tissue specimen is used to prepare a stained tissue section (the step (c) of the disclosed method). In one embodiment, the cleared and labeled tissue specimen may be directly used in the preparation of the stained tissue section. Alternatively, the cleared and labeled tissue specimen is pre-treated with water or saline such as phosphate buffered saline (a step referred to as reversion), usually at room temperature, to obtain a reversed tissue specimen, from which the stained tissue section may be prepared.

The stained tissue section is obtained according to methods well-known to one skilled in the art. In certain embodiments, a reversed tissue specimen is further fixed, dehydrated, infiltrated, and embedded as described above to form a tissue block, such as a FFPE-treated tissue block. The whole or part of the tissue block is then sliced into thin sections having a thickness of 0.5-10 µm, preferably 0.5-5 µm, by using a microtome, a slicing device with a blade to create micrometer thin slices of materials. Subsequently, each of the thin sections is mounted on a glass slide and stained according to staining methods known in the art, such that the overall structure of the tissue section (e.g., the distribution or organization of cells and extracellular matrix) and subtle morphological features of cells (e.g., the size of cell nucleus and the expression of specific proteins) can be well observed.

In certain embodiments, the tissue sections are stained with haematoxylin and eosin (H&E), which are two compounds coloring acidic structures (e.g., DNA in the cell nucleus and RNA in ribosomes and endoplasmic reticulum) purple or blue and coloring basic structures (e.g., most proteins in the cytoplasm, intracellular membrane, and extracellular matrix) pink or red, respectively. Therefore, H&E staining can stain cell nuclei and cytoplasm of cells in the tissue sections and allow localization of cell nuclei and cell membrane, which surrounds the cytoplasm. Briefly, the procedure of H&E staining begins with removing the embedding medium such as paraffin wax from one tissue section and rehydrating the section with decreasing concentrations of alcohol. The section is then stained with a haematoxylin solution, differentiated with an acid alcohol, and counterstained with an eosin Y solution. The H&E stained tissue section is further dehydrated with increasing concentrations of alcohol and dried before the second image acquisition of step (d).

In other embodiments, immunohistochemistry (IHC), which is based on antigen-antibody interactions, is used to prepare the stained tissue sections. Briefly, each tissue section is treated with at least one antibody specifically recognizing an antigen, particularly a protein characteristic of a disease. Typically, two types of antibodies, including a primary antibody and a secondary antibody, are used during IHC. The primary antibody detects the antigen in the tissue section. The second antibody is specific to the host of the primary antibody and is directly or indirectly conjugated to a reporter enzyme which catalyzes production of a colored compound upon the presence of a chromogenic substrate. Examples of such reporter enzyme include alkaline phosphatase (AP) and horseradish peroxidase (HRP). The chromogenic substrate of AP may be Fast Red or a combination of nitro blue tetrazolium (NBT) and 5-bromo-4-chloro-3-indolyl phosphate (BCIP). The chromogenic substrate of HRP may be 3,3'-diaminobenzidine (DAB) or aminoethyl carbazole (AEC). Accordingly, IHC can stain various cell substructures including cell nucleus, cytoplasm, and cell membrane through detection of specific antigens located in these cell substructures.

The second image acquisition of step (d) is to capture a reference 2D image of the stained tissue section. Typically, this step is performed by capturing a plurality of 2D microscopic images of a plurality of stained tissue sections with a wide-field imaging system, and then one of those 2D images is selected as the reference 2D image. The selection may be random or based on the expertise of a medical professional such as a pathologist. Generally, the reference 2D image shows, if any, at least one histopathological feature of a disease, for example, abnormal cell growth or tumor cell invasion into surrounding tissue.

The wide-field imaging system includes a wide-field light microscope, an image capture device connected to the wide-field light microscope, and a computer connected to the light microscope and the image capture device, both of which may be operated by the computer. While white light transmits through the stained tissue section, the absorptive stains such as H&E absorbed to the specimen allow observation of the morphological features of the specimen under the light microscope. The image capture device of the wide-field imaging system has similar elements as described for the image capture device of the fluorescence imaging system and thus can generate digital 2D images of the stained tissue sections. The digital 2D images may be stored in a memory unit of the computer.

Figure 2:
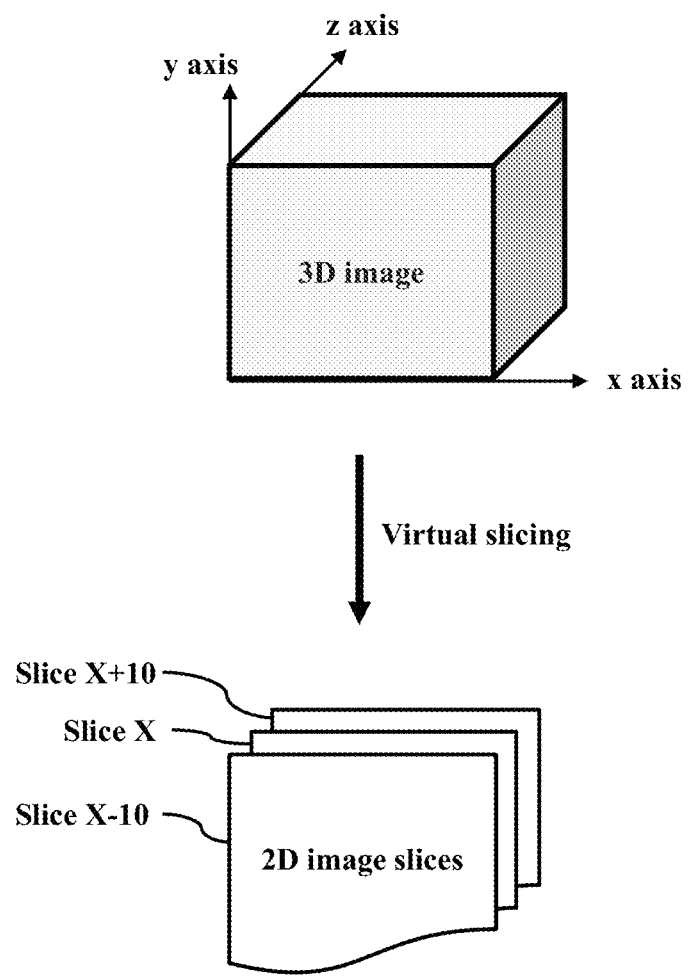
FIG. 2 illustrates virtual slicing of a 3D image of a tissue specimen to generate a series of 2D image slices including a corresponding 2D image slice (denoted as slice X) and at least two adjacent 2D image slices (denoted respectively as slice X−10 and X+10)

A matching (step (e) of the disclosed method) is subsequently performed between the reference 2D image and the 3D image of the tissue specimen so as to extract from the 3D image data a series of 2D image slices including a corresponding image slice, which corresponds to the reference 2D image. The matching is performed on a computer including a processor and a storage medium storing a plurality of instructions readable by the processor. The matching is implemented mainly by a feature detection algorithm, such as scale-invariant feature transform (SIFT) or speeded up robust features (SURF). The feature detection algorithm detects at least one keypoint of one image and extracts at least one feature vector by a defined descriptor. In some embodiments, by computing the minimum vector distance, the nearest neighbors between the feature vectors of the reference 2D image and each 2D image slice of the 3D image are identified while searching for an optimal feature loss, based on which a corresponding 2D image slice is found. As shown in FIG. 2, the 2D image slices are generated by virtual slicing, usually in the depth or z direction, of the 3D image into multiple virtual slices. Each image slice may be displayed on a monitor as a conventional 2D image showing a cross-sectional view of the imaged tissue specimen.

The term "feature vector" refers to a series of numbers containing information describing certain characteristics of an image or a virtual image slice. Thus, the feature vector disclosed herein includes a reference feature vector extracted from the reference 2D image and a corresponding feature vector extracted from one 2D image slice. In some embodiments, the feature vector is extracted based on the architectural features of a tissue specimen such as edges, corners, and blob patterns. Therefore, the feature vector disclosed herein describes at least one morphological feature that can be recognized in both the reference 2D image and the virtual 2D image slices. Examples of such morphological features include the shape or size of cells, the distribution or size of cell nuclei, the counts of cells or cell nuclei, the expression level of a biomolecule that is characteristic of a disease, the architecture of cells and extracellular matrix, or combinations thereof. Preferably, the reference feature vector or the corresponding feature vector describes a gross morphological feature such as cell nuclei distribution, so that the time for matching can be reduced.

The abovementioned matching step is repeated until the corresponding 2D image slice, for example, the slice X shown in FIG. 2, is obtained. The corresponding 2D image slice is one of the 2D image slices that most resembles or is least different in morphology from the reference 2D image comparing to other 2D image slices. In some embodiments, the corresponding 2D image slice and the reference 2D image have at least 90%, preferably 93%, and more preferably 95% of morphological similarity, the value of which may be determined by computing the feature vector distance. Once the corresponding 2D image slice is obtained, other 2D image slices that are adjacent in space to the corresponding 2D image slice can be collected. These adjacent 2D image slices and the corresponding 2D image slice collectively form a series of 2D image slices for assisting disease diagnosis that was traditionally simply based on the reference 2D image. In some embodiments, the adjacent 2D image slices include at least two 2D image slices that are parallel to the corresponding 2D image slice and individually at opposite sides of the corresponding 2D image slice, for example, the slice X−10 and slice X+10 as shown in FIG. 2. In some embodiments, the distance between the corresponding 2D image slice and the adjacent 2D image slice in the 3D image may range from 1 μm to 5 μm.

In certain embodiments, the matching may be further divided into the following sub-steps: (e1) channel selection, (e2) color deconvolution, (e3) color transformation, and (e4) comparison between the reference feature vector and the corresponding feature vector. Channel selection is based on the type of staining techniques used to prepare the stained tissue sections, for example, H&E staining or IHC. Color deconvolution is to separate the color information of a combination of two or more colors in multiple gray-scale images (i.e., the 2D image of the stained tissue section) into different channels, such that visualization and quantification of each type of staining is possible even in areas where multiple stains are co-localized. Color transformation is optional and is applied for better visual comparison by converting the colors of the reference 2D image to those of the series of 2D image slices. Steps (e1) to (e3) may be performed by using open source software, for example, ImageJ (National Institutes of Health). Step (e4) may be carried out by the aforementioned feature detection algorithms.

After extraction of the series of 2D image slices, at least one pathological score is determined for each 2D image slice in the series of 2D image slices and a report of the presence or absence and the extent of the disease is generated based on the multiple pathological scores (step (f) of the disclosed method). The process of determining pathological scores and generating a diagnostic report may be implemented on a computer by using suitable algorithms. The pathological score is a value indicating the extent to which a disease-related abnormality can be found in a 2D image slice or a predetermined region of the 2D image slice. In one embodiment, the pathological score is determined by measuring the expression level of a protein that is characteristic of a disease or the immune status of the subject to be diagnosed. The protein expression level is commonly used in evaluation of diseases or therapies because it is closely related to the initiation and progress of a disease and is also affected by an individual's immune activities and therapeutic interventions such as immunotherapy. Said proteins may be marker proteins that are specific for cancers, for example, estrogen receptor (ER), progesterone receptor (PR), and human epidermal growth factor 2 (HER2) for breast cancer; thyroid transcription factor-1 (TTF1) for pulmonary and thyroid adenocarcinoma; and nuclear antigen Ki-67, pan-cytokeratin (PanCK), tumor protein 63 (also called p63), programmed death-ligand 1 (PD-L1) for various cancers. Said proteins may also be proteins expressed by immune cells such as cluster of differentiation 4 (CD4), cluster of differentiation 8 (CD8), and cluster of differentiation (CD45). Protein expression levels can be measured by determining the density of a fluorescence probe, such as a fluorophore-conjugated antibody which recognizes the marker protein(s), in each 2D image slice.

In another embodiment, the pathological score is determined by measuring a proportion of cells with abnormal morphology relative to total cells in one 2D image slice. The expression of "abnormal morphology" means that the appearance of a plurality of cells in a tissue specimen is significantly distinct from the appearance of cells in a control tissue specimen from a healthy subject. Examples of the "abnormal morphology" of cells include abnormal shapes of cells, an abnormal arrangement of cells such as formation of a large cell aggregate, and an abnormal nuclear-cytoplasmic ratio (N:C ratio) of cells.

The pathological scores obtained from the series of 2D image slices are the basis for assisting the generation of a histopathological report. Traditionally, the results of histopathological examination merely rely on 2D images of the stained tissue sections that show abnormal tissue morphology. In contrast, the method disclosed herein utilizes said pathological scores to verify the histopathological results. The pathological scores vary greatly among tissue specimens collected from diseased and non-diseased persons. A pathological score indicating the presence or extent of a disease must fall within the range of a self-defined or widely used disease standard. The disease standard may be expressed as a numerical value or a numerical range, which is determined based on tissue specimens from diseased and non-diseased persons. In some embodiments, the presence and extent of a disease is reported when the pathological score is above or below a numerical value or within a numerical range. Moreover, in certain embodiments, the presence and extent of a disease is reported when the difference between the pathological scores of any two of the series of the 2D image slices is within a predetermined range and thus considered statistically non-significant. For example, the differences between the pathological scores of slice X and slice X+10, slice X and slice X−10, and slice X+10 and slice X−10 as shown in FIG. 2 are all within a 90%, preferably 95% confidence interval for a mean of the pathological scores ($p>0.05$) when a statistical analysis such as student's t test is performed. The statistical analysis may be other statistical methods such as analysis of variance (ANOVA). Since the 2D image slices are extracted from the 3D image of the whole tissue specimen, which has not been sliced at all or has been subjected to very few rounds of slicing, the pathological scores obtained from the 2D image slices are least interfered by the sample preparation process and thus are more reliable. Therefore, the method disclosed herein can increase the accuracy of histopathological diagnosis.

Example 1

Diagnostic Report Based on a Breast Tissue Specimen

A fresh breast tissue specimen was collected from a female patient suffering from breast cancer. The tissue specimen, first fixed with 4% formaldehyde, was then permeated with 0.1-1% Triton X-100. Subsequently, the tissue specimen was stained with SYTO 16 and DiD to label cell nucleus and cell membrane, respectively. Each labeling was carried out at room temperature for 8 hours, followed by labeling of Ki-67 by treating the specimen with rabbit anti-Ki-67 primary antibody (VENTANA) at room temperature for about 10 hours and with Alexa Fluor 405-conjugated goat anti-rabbit IgG secondary antibody (Thermo Fisher Scientific) at 4° C. for about 16 hours. The labeled specimen was then immersed in an aqueous clearing agent with a refractive index of about 1.45 at room temperature for about 3 hours to obtain a cleared and labeled specimen. The aqueous clearing agent was prepared by mixing 30-50% meglumine diatrizoate and 10-30% triethanolamine in distilled water. The cleared and labeled tissue specimen, with a thickness of about 200 μm, was imaged from the top surface to the bottom surface with a LSCM system (LSM780; Zeiss) to obtain about a hundred successive 2D images of the specimen that were then used to generate a 3D composite image of the specimen. These images were acquired by excitation and emission at 405 nm and 435 nm, respectively, for detection of Alexa Fluor 405; at 480 nm and 525 nm, respectively, for detection of SYTO 16; and at 638 nm and 700 nm for detection of DiD. The lateral resolution (in the x and y directions) was less than 1 μm and the axial resolution (in the z direction) was less than 2 μm.

Figure 3A:
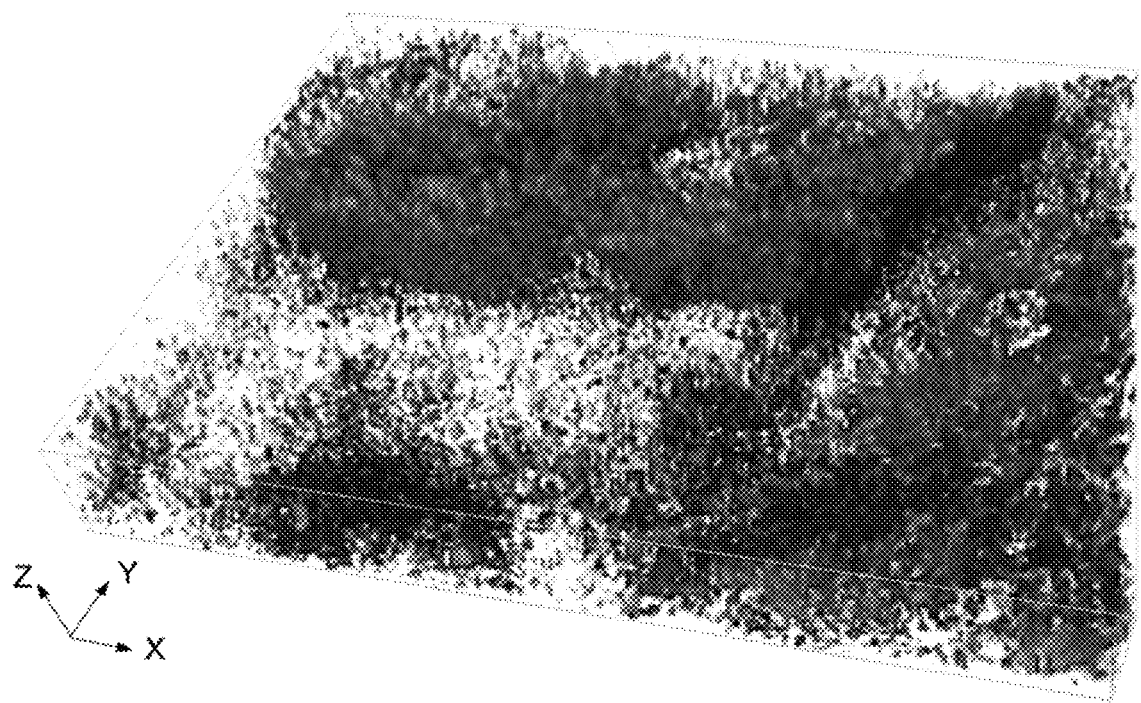
FIG. 3A is a 3D image of a breast tissue specimen collected from a breast cancer patient; the specimen was labeled with three fluorescent probes.

FIG. 3A shows a 3D image of the breast tissue specimen, in which the fluorescent signals of SYTO 16 (indicating cell nuclei) and DiD (indicating cell membrane) were merged. The 3D image was generated by stitching the successive 2D images together using trilinear interpolation and visualized by ray casting volume rendering. Since the labeled cell substructures throughout the whole specimen were imaged and a 3D model of the specimen was reconstructed (i.e., the 3D image), pathological analysis of the specimen at cellular level was achievable subsequently.

Figure 3B:
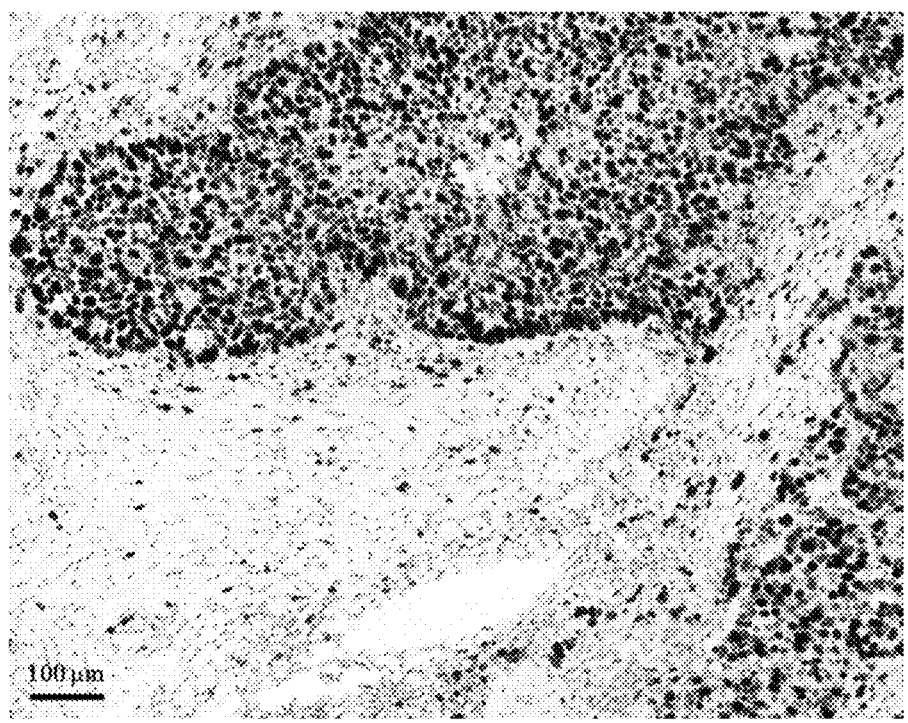
FIG. 3B is a reference 2D image of a stained tissue section prepared from the breast tissue specimen indicated in the description of FIG. 3A; the scale bar in FIG. 3B represents 100 μm.

After imaged, the specimen was incubated in distilled water at room temperature for about 10 minutes to obtain a reversed specimen, which was then stripped of the antibodies and fluorescent dyes. Subsequently, the specimen was dehydrated, embedded in paraffin, and sliced into a plurality of about 3 μm-thick thin sections. The sections were stained by IHC, including using rabbit anti-Ki-67 primary antibody (VENTANA) at 4° C. for about 12 hours and HRP-conjugated goat anti-rabbit IgG secondary antibody (Thermo Fisher Scientific) at room temperature for 30 minutes to probe Ki67, followed by treating the sections with DAB and haematoxylin at room temperature for 3-5 minutes to stain the Ki-67-expressed regions and cell nuclei, respectively. The stained sections were imaged with Aperio series of Leica biosystem, a digital slide scanning system. The obtained 2D images were examined so that a reference 2D image (FIG. 3B) displaying formation of a larger cell aggregate (a histological sign of breast cancer) was chosen for matching.

Figure 3C:
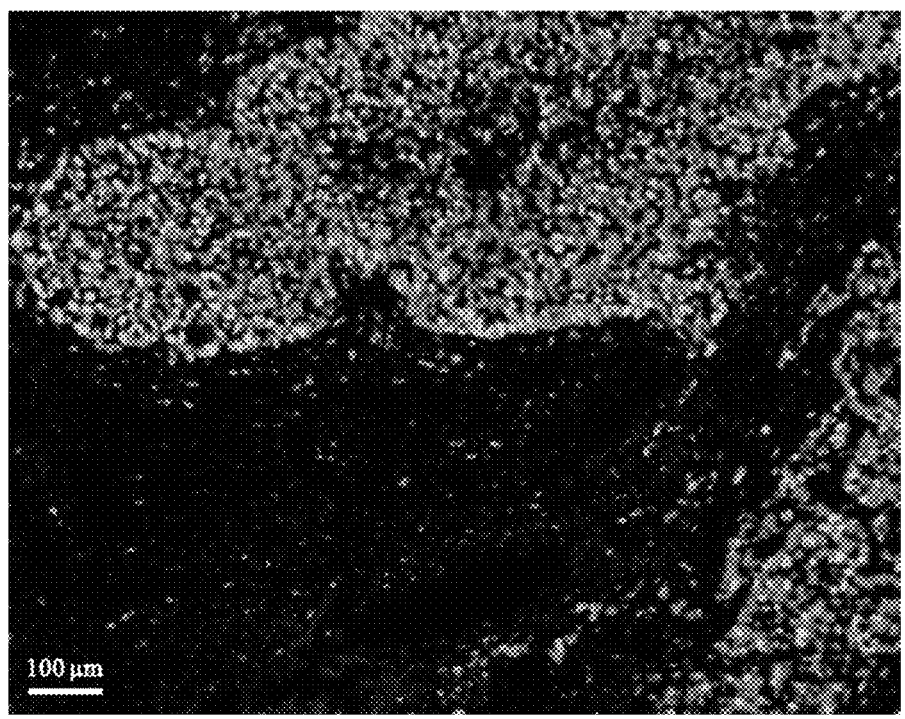
FIG. 3C is a color-transformed output image of the reference 2D image shown in FIG. 3B; the scale bar in FIG. 3C represents 100 μm.
Figure 3D:
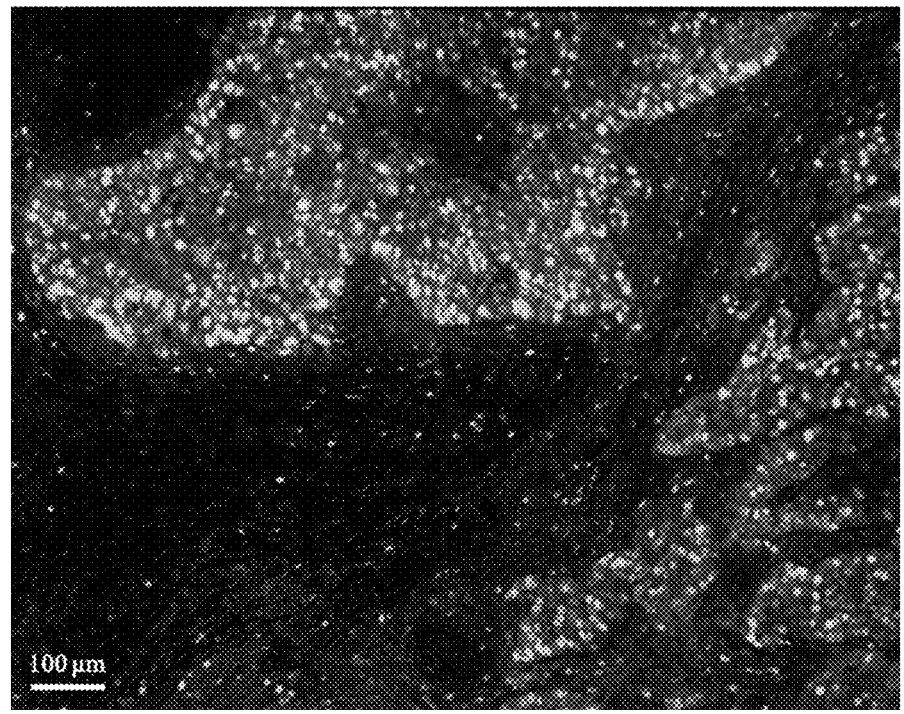
FIG. 3D is a corresponding 2D image slice (denoted as slice X) extracted from the 3D image shown in FIG. 3A and matched to FIG. 3C; the scale bar in FIG. 3D represents 100 μm.
Figure 3E:
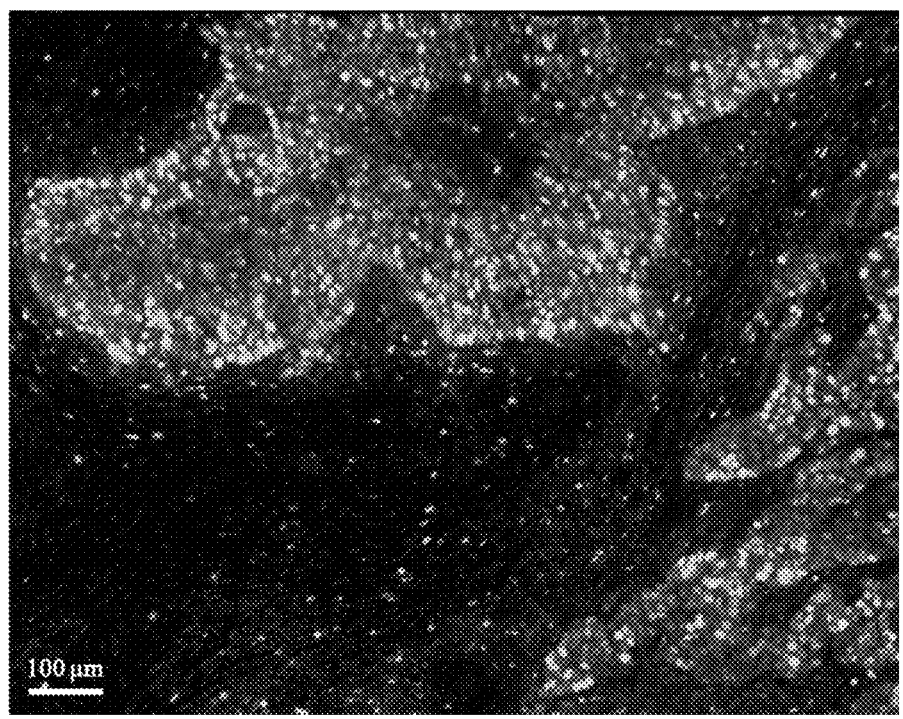
FIG. 3E is one 2D image slice (denoted as slice X−10) extracted from the 3D image shown in FIG. 3A; in the 3D image, the slice X−10 was adjacent to and at one side of the slice X (FIG. 3D); the scale bar in FIG. 3E represents 100 μm.
Figure 3F:
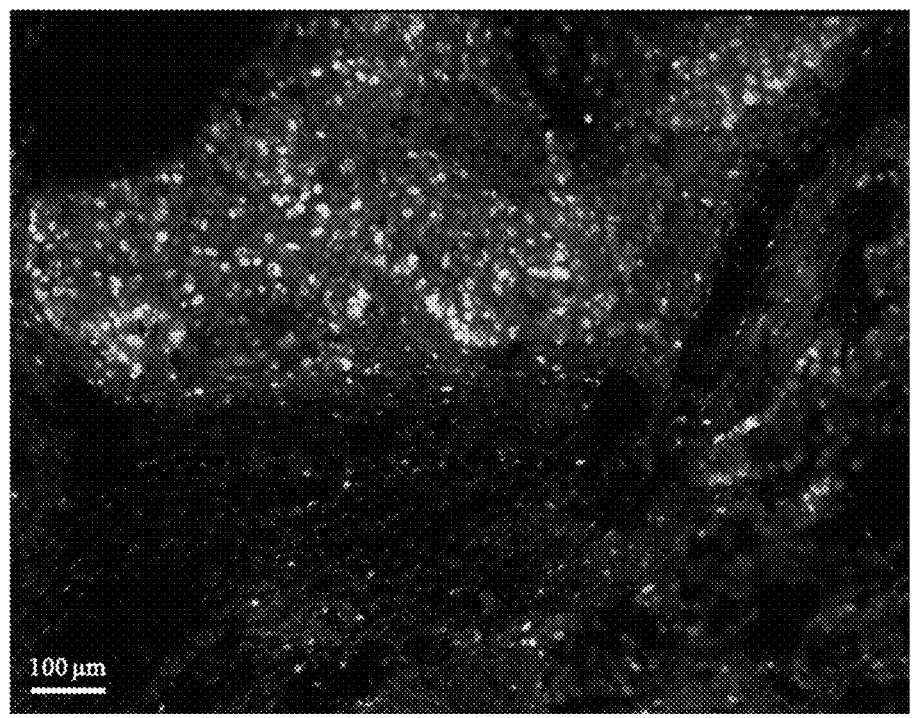
FIG. 3F is another 2D image slice (denoted as slice X+10) extracted from the 3D image shown in FIG. 3A; in the 3D image, the slice X+10 was adjacent to and at the other side of the slice X (FIG. 3D) that was opposite to the side where the slice X−10 (FIG. 3E) was positioned; the scale bar in FIG. 3F represents 100 μm.

Matching was performed with a python-based SIFT algorithm and ImageJ. In brief, IHC channel was specified, and color deconvolution and color transformation were applied to FIG. 3B. FIG. 3C is the color transformed output image of FIG. 3B. By matching FIG. 3C with the 3D image (FIG. 3A), a corresponding 2D image slice (FIG. 3D; denoted as slice X), where tissue architecture most resembled that shown in FIG. 3C, was extracted from the 3D image. Also, as shown in FIG. 3E and FIG. 3F, two additional 2D image slices (denoted as slice X−10 and X+10, respectively) that were adjacent to two sides of the slice X were extracted from the 3D image. The distance between the slice X and the slice X−10 or slice X+10 in the 3D image was 1 μm. With reference to the three image slices, Ki-67 antibody density (TABLE 1) can be determined as the ratio of the counts of cells labeled with Alexa Fluor 405 (i.e., counts of Ki-67 positive cells) to the counts of cells labeled with SYTO 16 (i.e., counts of cell nuclei). The Ki-67 antibody density is a measure of the expression level of the breast cancer marker protein Ki-67, and thus can be used as a pathological score to assess the presence and extent of breast cancer.

TABLE 1

|  | Cell nuclei (counts) | Ki-67 positive cells (counts) | Ki-67 Antibody Density |
|---|---|---|---|
| Slice X − 10 | 2969 | 893 | 30.1% |
| Slice X | 3104 | 968 | 31.2% |
| Slice X + 10 | 2179 | 677 | 31.1% |

According to TABLE 1, the Ki-67 antibody density of the slice X was 31.2%, which was slightly above a cutoff point of 30%. This cutoff point is an important factor in breast cancer diagnostic and also serves as a predictor of favorable chemotherapy response in breast cancer. Moreover, the Ki-67 antibody densities of the slice X−10 and X+10 were 30.1% and 31.1%, respectively. Since the values of Ki-67 antibody density were all above 30% and not statistically different to each other, the tissue specimen with a high Ki-67 index was reported to be derived from a breast cancer patient, who was further advised to receive chemotherapy.

Example 2

Diagnostic Report Based on a Lung Tissue Specimen

A fresh lung tissue specimen was collected from a patient suffering from lung cancer. The tissue specimen, first fixed with 4% formaldehyde, was then permeated with 0.1-1%

Triton X-100. Subsequently, the tissue specimen was stained with SYTO 16 and DiD to label cell nucleus and cell membrane, respectively. Each labeling was carried out at room temperature for 6-8 hours. The labeled specimen was then immersed in an aqueous clearing agent with a refractive index of about 1.45 at room temperature for about 3 hours to obtain a cleared and labeled specimen. The aqueous clearing agent was prepared by mixing 30-50% meglumine diatrizoate and 10-30% triethanolamine in distilled water. The cleared and labeled tissue specimen, with a thickness of about 200 µm, was imaged from the top surface to the bottom surface with a LSCM system (LSM780; Zeiss) to obtain about a hundred successive 2D images of the specimen that were then used to generate a 3D composite image of the specimen. These images were acquired by excitation and emission at 480 nm and 525 nm, respectively, for detection of SYTO 16; and at 638 nm and 700 nm for detection of DiD. The lateral resolution (in the x and y directions) was less than 1 µm and the axial resolution (in the z direction) was less than 2 µm.

Figure 4A:
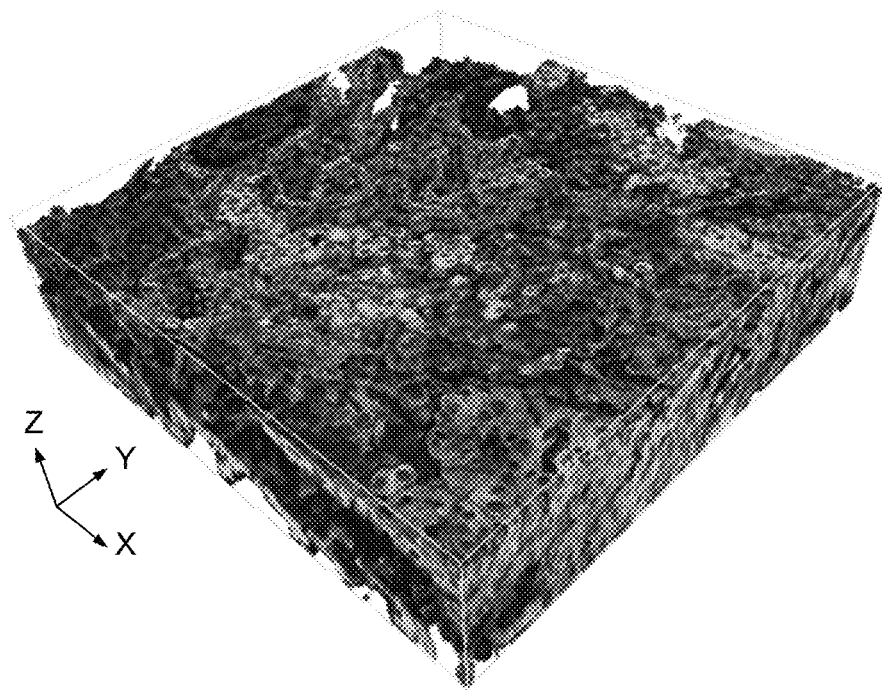
FIG. 4A is a 3D image of a lung tissue specimen collected from a lung cancer patient; the specimen was labeled with two fluorescent probes.

FIG. 4A shows a 3D image of the lung tissue specimen, in which the fluorescent signals of SYTO 16 and DiD were merged. The 3D image was generated by stitching the successive 2D images together using trilinear interpolation and visualized by ray casting volume rendering.

Figure 4B:
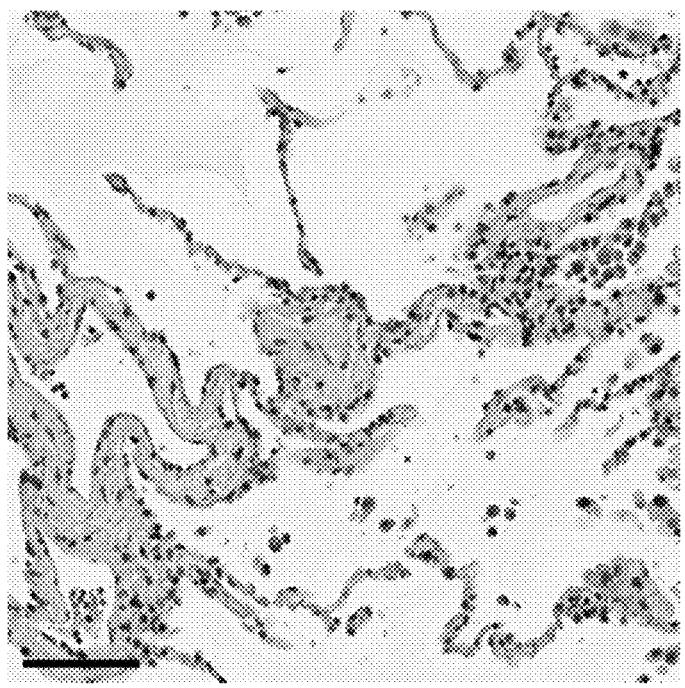
FIG. 4B is a reference 2D image of a stained tissue section prepared from the lung tissue specimen indicated in the description of FIG. 4A; the scale bar in FIG. 4B represents 100 μm.

After imaged, the specimen was incubated in distilled water at room temperature for about 10 minutes to obtain a reversed specimen, which was then stripped of the fluorescent dyes. Subsequently, the specimen was dehydrated, embedded in paraffin, and sliced into a plurality of about 3 µm-thick thin sections. The sections were stained by hematoxylin and eosin at room temperature for 3-5 minutes to stain the cell nucleus and cytoplasm, respectively. The stained sections were imaged with Aperio series of Leica biosystem. The obtained 2D images were examined so that a reference 2D image (FIG. 4B) displaying formation of a larger cell aggregate (a histological sign of lung cancer) was chosen for matching.

Figure 4C:
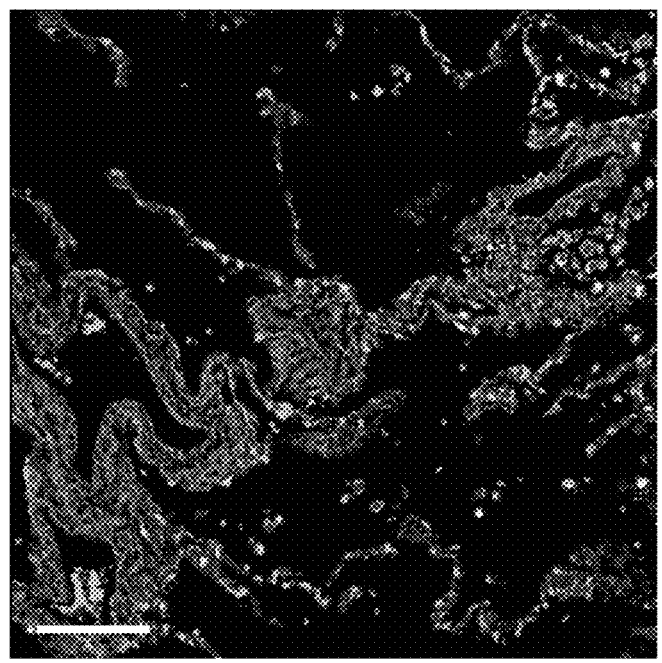
FIG. 4C is a color-transformed output image of the reference 2D image shown in FIG. 4B; the scale bar in FIG. 4C represents 100 μm.
Figure 4D:
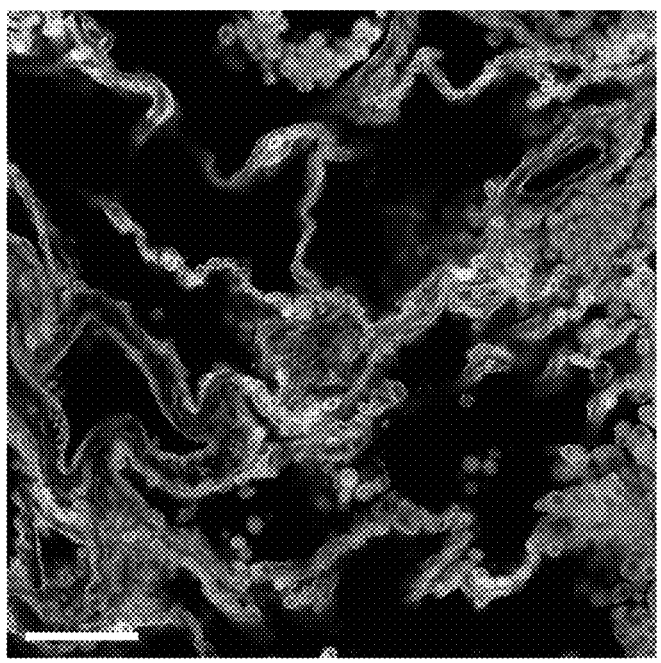
FIG. 4D is a corresponding 2D image slice (denoted as slice X) extracted from the 3D image shown in FIG. 4A and matched to FIG. 4C; the scale bar in FIG. 4D represents 100 μm.
Figure 4E:
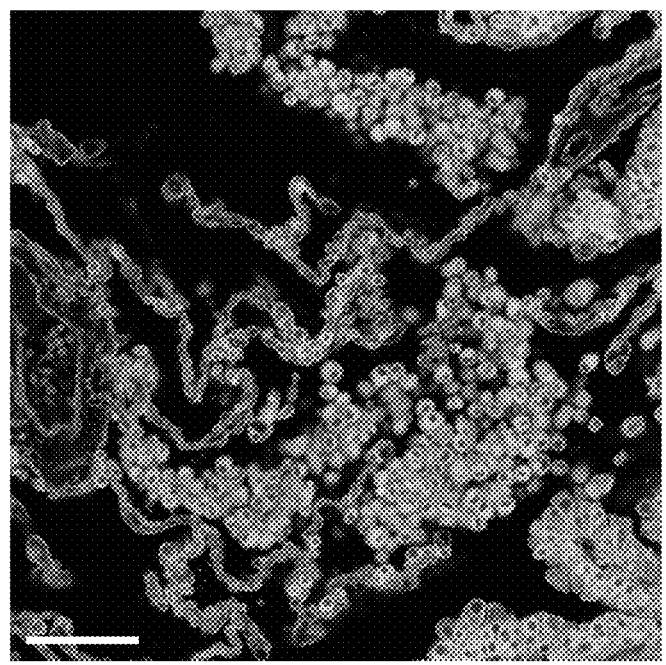
FIG. 4E is one 2D image slice (denoted as slice X−10) extracted from the 3D image shown in FIG. 4A; in the 3D image, the slice X−10 was adjacent to and at one side of the slice X (FIG. 4D); the scale bar in FIG. 4E represents 100 μm.
Figure 4F:
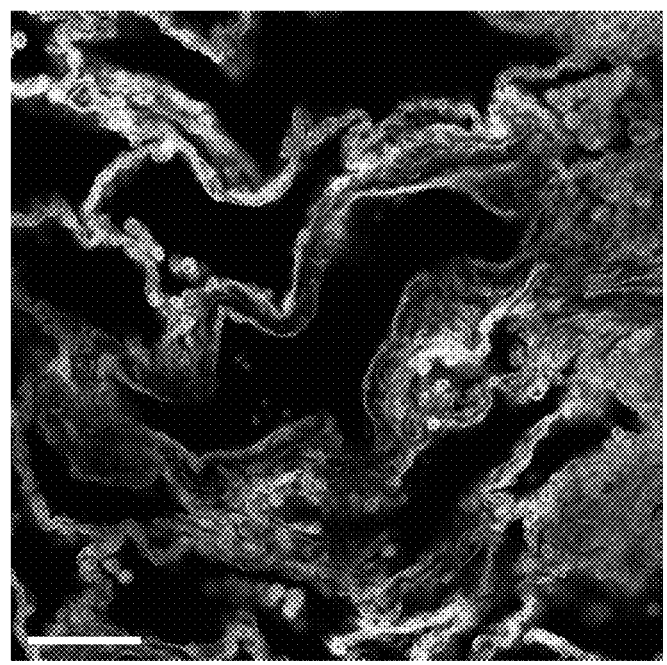
FIG. 4F is another 2D image slice (denoted as slice X+10) extracted from the 3D image shown in FIG. 4A; in the 3D image, the slice X+10 was adjacent to and at the other side of the slice X (FIG. 4D) that was opposite to the side where the slice X−10 (FIG. 4E) was positioned; the scale bar in FIG. 4F represents 100 μm.

Matching was performed with a python-based SIFT algorithm and ImageJ. In brief, H&E channel was specified, and color deconvolution and color transformation were applied to FIG. 4B. FIG. 4C is the color transformed output image of FIG. 4B. By matching FIG. 4C with the 3D image (FIG. 4A), a corresponding 2D image slice (FIG. 4D; denoted as slice X), where tissue architecture most resembled that shown in FIG. 4C, was extracted from the 3D image. Also, as shown in FIG. 4E and FIG. 4F, two additional 2D image slices (denoted as slice X-10 and X+10, respectively) that were adjacent to two sides of the slice X were extracted from the 3D image. The distance between the slice X and the slice X-10 or slice X+10 in the 3D image was 3 µm. With reference to the three image slices, percentage of tumor region (TABLE 2) can be determined as the ratio of the area of tumor region detected with a deep learning algorithm to the area of the image slice. The percentage of tumor region is a measure of tumor progression and is a key factor in the TNM cancer staging system. Thus, it can be used as a pathological score to assess the presence and extent of lung cancer.

TABLE 2

| | Percentage of Tumor region |
|---|---|
| Slice X − 10 | 27% |
| Slice X | 16% |
| Slice X + 10 | 52% |

According to TABLE 2, the tumor region in the slice X-10 or slice X+10 accounted for 27% or 52%, respectively, both of which were much higher than the tumor region in the slice X (16%). The results indicated that the tumor stage determined based only on the reference 2D image would have probably been underestimated, and that such underestimation can be prevented by obtaining additional pathological information from the suitable 2D image slices, which are extracted from the 3D image of the whole tissue specimen. In other words, the method disclosed herein facilitates early detection of tumor progression and early treatment of cancers.

The method of the present invention helps pathologists make more accurate diagnostic decisions by generating a 3D image of the whole tissue specimen and extracting from the 3D image a series of 2D image slices to obtain reliable pathological scores that can be used to verify histopathological results. Therefore, the method can be employed in determination of the presence and extent of diseases such as cancers and identification of disease subtypes in patients. Moreover, the method can be applied in prediction of the development of a disease, selection of appropriate medical treatments, and assessment of the efficacy of therapies such as a radiotherapy, chemotherapy, immunotherapy and surgery.

What is claimed is:

1. A method for analyzing a tissue specimen, comprising the steps of:
   (a) treating a tissue specimen from a subject with an aqueous clearing agent and with at least two fluorescent probes for labeling cell membrane and cell nuclei so as to obtain a cleared and labeled tissue specimen;
   (b) imaging the cleared and labeled tissue specimen to generate a three-dimensional (3D) image of the tissue specimen;
   (c) preparing a stained tissue section from the cleared and labeled tissue specimen;
   (d) capturing a reference two-dimensional (2D) image of the stained tissue section;
   (e) matching the reference 2D image with the 3D image to extract from the 3D image a series of 2D image slices, wherein one 2D image slice in the series of 2D image slices is a corresponding 2D image slice that corresponds to the reference 2D image, and the corresponding 2D image slice, compared to all other 2D image slices in the series of 2D image slices, is least different from the reference 2D image in terms of morphology; and
   (f) determining at least one pathological score for each 2D image slice in the series of 2D image slices and reporting the presence or absence and the extent of a disease based on the pathological scores.

2. The method of claim 1, wherein the aqueous clearing agent has a refractive index of 1.33-1.55.

3. The method of claim 1, wherein the aqueous clearing agent comprises an ingredient selected from the group consisting of glycerol, histodenz, formamide, triethanolamine, meglumine diatrizoate, and combinations thereof.

4. The method of claim 1, wherein the tissue specimen of step (a) has a thickness of at least 200 µm.

5. The method of claim 1, wherein the 3D image is a 3D composite image generated from a plurality of successive 2D images of the cleared and labeled tissue specimen.

6. The method of claim 5, wherein the plurality of successive 2D images are captured using a fluorescence imaging system comprising a laser scanning confocal microscope.

7. The method of claim 1, wherein in step (a) the tissue specimen is further treated with another fluorescent probe to label at least one biomolecule or at least one organelle.

8. The method of claim 7, wherein the biomolecule is a protein characteristic of the disease.

9. The method of claim 7, wherein the biomolecule is a protein selected from the group consisting of estrogen receptor (ER), progesterone receptor (PR), human epidermal growth factor 2 (HER2), thyroid transcription factor-1 (TTF1), Ki-67, pan-cytokeratin (PanCK), p63, programmed death-ligand 1 (PD-L1), CD4, CD8, CD45, and combinations thereof.

10. The method of claim 1, wherein the tissue specimen of step (a) is fresh or further fixed.

11. The method of claim 1, wherein the cleared and labeled tissue specimen in step (c) is treated with water or saline to obtain a reversed tissue specimen for preparation of the stained tissue section.

12. The method of claim 1, wherein in step (c) the stained tissue section is prepared by staining a plurality of tissue sections obtained from the cleared and labeled tissue specimen.

13. The method of claim 12, wherein the staining is accomplished by haematoxylin and eosin staining or immunohistochemistry.

14. The method of claim 1, wherein the matching of step (e) is accomplished by comparing a reference feature vector of the reference 2D image to a corresponding feature vector of each 2D image slice in the series of 2D image slices.

15. The method of claim 14, wherein the reference feature vector or the corresponding feature vector describes cell shape, cell nuclei distribution, or combinations thereof.

16. The method of claim 1, wherein the pathological score is determined by measuring a proportion of cells with abnormal morphology relative to total cells in one 2D image slice.

17. The method of claim 1, wherein the pathological score is determined by measuring an expression level of a protein characteristic of the disease.

18. The method of claim 1, wherein the presence of the disease is reported when the difference between the pathological scores of any two 2D image slices in the series of 2D image slices is within a predetermined range.

19. The method of claim 1, wherein the disease is neoplasm.

20. The method of claim 19, wherein the neoplasm is selected from the group consisting of breast cancer, lung cancer, gastric cancer, liver cancer, gallbladder cancer, pancreatic cancer, colon cancer, colorectal cancer, prostate cancer, cervical cancer, ovarian cancer, kidney cancer, bladder cancer, glioma, retinoblastoma, melanoma, and head and neck cancers.

* * * * *